United States Patent
Whitehurst et al.

(10) Patent No.: US 7,925,353 B1
(45) Date of Patent: *Apr. 12, 2011

(54) TREATMENT OF MOVEMENT DISORDERS WITH DRUG THERAPY

(75) Inventors: Todd K. Whitehurst, Santa Clarita, CA (US); James P. McGivern, Stevenson Ranch, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/374,799

(22) Filed: Mar. 13, 2006

Related U.S. Application Data

(63) Continuation of application No. 10/810,091, filed on Mar. 25, 2004, now Pat. No. 7,155,279.

(60) Provisional application No. 60/458,451, filed on Mar. 28, 2003.

(51) Int. Cl.
*A61N 1/08* (2006.01)
*A61N 1/00* (2006.01)

(52) U.S. Cl. .................................. 607/45; 607/2; 607/3

(58) Field of Classification Search .............. 607/3, 45, 607/46, 48, 116–118, 49
See application file for complete search history.

(56) References Cited

U.S. PATENT DOCUMENTS

| | | | |
|---|---|---|---|
| 4,702,254 A | 10/1987 | Zabara | |
| 4,867,164 A | 9/1989 | Zabara | |
| 5,025,807 A | 6/1991 | Zabara | |
| 5,193,539 A | 3/1993 | Schulman et al. | |
| 5,193,540 A | 3/1993 | Schulman et al. | |
| 5,304,206 A | 4/1994 | Baker, Jr. et al. | |
| 5,312,439 A | 5/1994 | Loeb | |
| 5,683,422 A | 11/1997 | Rise | |
| 5,711,316 A | 1/1998 | Elsberry et al. | |
| 5,713,923 A * | 2/1998 | Ward et al. | 607/3 |
| 5,716,377 A | 2/1998 | Rise et al. | |
| 5,792,186 A | 8/1998 | Rise | |

(Continued)

FOREIGN PATENT DOCUMENTS

WO    WO-85/01213 A1    3/1985

(Continued)

OTHER PUBLICATIONS

Cameron, et al. "Micromodular Implants to Provide Electrical Stimulation of Paralyzed Muscles and Limbs", IEEE Transactions on Biomedical Engineering, vol. 44, No. 9, (Sep. 1997), pp. 781-790.

(Continued)

*Primary Examiner* — Carl H Layno
*Assistant Examiner* — Gary A Porter, Jr.
(74) *Attorney, Agent, or Firm* — Henricks, Slavin & Holmes LLP

(57) ABSTRACT

Introducing one or more stimulating drugs to the vagus nerve and/or one or more branches of the vagus nerve to treat movement disorders uses at least one implantable system control unit (SCU) with an implantable pump with at least one infusion outlet. Optional electrical stimulation may additionally be supplied by an implantable signal/pulse generator (IPG) with one or more electrodes. In certain embodiments, a single SCU provides one or more stimulating drugs and the optional electrical stimulation. In some embodiments, one or more sensed conditions are used to adjust stimulation parameters.

20 Claims, 8 Drawing Sheets

U.S. PATENT DOCUMENTS

| | | | |
|---|---|---|---|
| 5,832,932 A * | 11/1998 | Elsberry et al. | 128/898 |
| 5,833,709 A | 11/1998 | Rise et al. | |
| 6,051,017 A | 4/2000 | Loeb et al. | |
| 6,094,598 A * | 7/2000 | Elsberry et al. | 607/116 |
| 6,104,956 A | 8/2000 | Naritoku et al. | |
| 6,178,349 B1 * | 1/2001 | Kieval | 607/3 |
| 6,205,359 B1 | 3/2001 | Boveja | |
| 6,227,203 B1 | 5/2001 | Rise et al. | |
| 6,356,784 B1 * | 3/2002 | Lozano et al. | 607/2 |
| 6,356,788 B2 | 3/2002 | Boveja | |
| 6,374,140 B1 * | 4/2002 | Rise | 607/45 |
| 6,464,687 B1 | 10/2002 | Ishikawa et al. | |
| 6,671,555 B2 * | 12/2003 | Gielen et al. | 607/45 |
| 6,788,975 B1 | 9/2004 | Whitehurst et al. | |
| 7,003,352 B1 | 2/2006 | Whitehurst | |
| 7,151,961 B1 | 12/2006 | Whitehurst et al. | |
| 2002/0013612 A1 * | 1/2002 | Whitehurst | 607/45 |
| 2002/0086343 A1 * | 7/2002 | Cameron et al. | 435/20 |
| 2002/0103516 A1 | 8/2002 | Patwardhan et al. | |
| 2002/0111601 A1 * | 8/2002 | Thompson | 604/514 |
| 2003/0036780 A1 * | 2/2003 | Barrett et al. | 607/45 |
| 2006/0241717 A1 | 10/2006 | Whitehurst et al. | |

FOREIGN PATENT DOCUMENTS

| | | |
|---|---|---|
| WO | WO-98/37926 A1 | 9/1998 |
| WO | WO-98/43700 A1 | 10/1998 |
| WO | WO-98/43701 A1 | 10/1998 |
| WO | WO-00/01320 A3 | 1/2000 |

OTHER PUBLICATIONS

Handforth, et al., "Effect of Vagus Nerve Stimulation on Essential Tremor", Neurology, vol. 54 Suppl. 3, (2000), p. A238.

Handforth, et al., "Suppression of Harmaline-Induced Tremor in Rats by Vagus Nerve Stimulation", Movement Disorders, vol. 16(1), (Jan. 2001), pp. 84-88.

Walker, et al., "Regulation of Limbic Motor Seizures by GABA and Glutamate Transmission in Nucleus Tractus Solitarius", Epilepsia, vol. 40(8), (Aug. 1999), pp. 1051-1057.

Whitehurst, McGivern, and Kuzma inventors for AB-116U; U.S. Appl. No. 10/081,820, filed Feb. 19, 2002; entitled "Fully Implantable Miniature Neurostimulator for Vagus Nerve Stimulation".

* cited by examiner

TREATMENT OF MOVEMENT DISORDERS WITH DRUG THERAPY

The present application is a continuation application of U.S. application Ser. No. 10/810,091, filed Mar. 25, 2004, which application is now U.S. Pat. No. 7,155,279, issued Dec. 26, 2006, and which application claims the benefit of U.S. Provisional Patent Application Ser. No. 60/458,451, filed 28 Mar. 2003, which application is incorporated herein by reference.

FIELD OF THE INVENTION

The present invention generally relates to implantable drug delivery systems and methods, and more particularly relates to utilizing such devices to deliver one or more therapeutic drugs, possibly combined with electrical stimulation, to a vagus nerve as a treatment for movement disorders.

BACKGROUND OF THE INVENTION

Movement disorders are neurologic syndromes characterized by either an excess or a paucity of movement. These disorders affect approximately two million Americans, including over one million suffering from benign essential tremor, and half a million suffering from Parkinson's Disease. A substantial percentage of those afflicted with movement disorders experience a significant decrease in quality of life, suffering such problems as incapacitating tremor, limited mobility, bradykinesia (difficulty consciously initiating movement), dysarthria (difficulty with speech), and consequent social isolation. The etiology of many movement disorders, e.g., benign essential tremor, is poorly understood. For other movement disorders, e.g., Parkinson's disease, the mechanism of the disorder and even the brain cells affected have been identified, but even with optimal care the disease may not be reversed and may even continue to progress.

Parkinson's Disease is caused by a gradual loss of dopaminergic (i.e., dopamine-secreting) neurons in the substantia nigra. Consequently, levels of dopamine decrease in the striatum (i.e., the putamen and the caudate nucleus). Although dopamine has both excitatory and inhibitory effects on the striatum, the predominant effect of the loss of dopamine is decreased inhibition (by GABA) of the internal segment of the globus pallidus. This leads to increased GABA output from the internal segment of the globus pallidus, which inhibits the ventrolateral thalamus. This leads in turn to decreased inhibition of (and ultimately decreased control over) the motor cortex. The subthalamic nucleus appears to increase its activity in Parkinson's Disease as well, and this is believed to contribute to the symptoms of the disease.

Essential Tremor (ET), a.k.a. Benign Essential Tremor, is the most common movement disorder. It is a syndrome characterized by a slowly progressive postural and/or kinetic tremor, usually affecting both upper extremities. The prevalence of ET in the US is estimated at 0.3-5.6% of the general population. A 45-year study of ET in Rochester, Minn. reported an age- and gender-adjusted prevalence of 305.6 per 100,000 and an incidence of incidence of 23.7 per 100,000.

ET affects both sexes equally. The prevalence of ET increases with age. There are bimodal peaks of onset—one in late adolescence to early adulthood and a second peak in older adulthood. The mean age at presentation is 35-45 years. ET usually presents by 65 years of age and virtually always by 70 years. Tremor amplitude slowly increases over time. Tremor frequency decreases with increasing age. An 8-12 Hz tremor is seen in young adults and a 6-8 Hz tremor is seen in the elderly. Although ET is progressive, no association has been found between age of onset and severity of disability.

Mortality rates are not increased in ET. However, disability from ET is common. Significant changes in livelihood and socializing are reported by 85% of individuals with ET, and 15% report being seriously disabled due to ET. Decreased quality of life results from both loss of function and embarrassment. In a study of hereditary ET, 60% did not seek employment; 25% changed jobs or took early retirement; 65% did not dine out; 30% did not attend parties, shop alone, partake of a favorite hobby or sport, or use public transportation; and 20% stopped driving.

There are no known pathological findings associated with ET. However, it has been hypothesized that ET is the result of an abnormally functioning central oscillator that is located in Guillain Mollaret triangle near the brainstem and involves the inferior olivary nucleus. In addition, there is probable involvement of cerebellar-brainstem-thalamic-cortical circuits.

When harmaline, a Monoamine Oxidase (MAO) inhibitor, is administered to primates with ventromedial tegmental tract or lateral cerebellum lesions, an ET-like tremor is produced. In these animals, inferior olivary nucleus neurons fire synchronously at the tremor frequency. Hypermetabolism has also been demonstrated in the inferior olivary nuclei of rats and cats with harmaline-induced tremor.

In patients with ET, studies have identified increased glucose consumption in the medulla. An increase in medullary regional cerebral blood flow in subjects with ET occurred only after administration of ethanol, and showed bilateral overactivity of cerebellar circuitry.

Patients suffering from tremor (e.g., due to ET or Parkinson's disease) and other symptoms may undergo surgery to lesion a part of the brain (e.g., the ventral intermediate (Vim) nucleus of the thalamus, the internal globus pallidus (Gpi), or the subthalamic nucleus (STN)), which may afford some relief. However, lesions are irreversible, and may lead to side effects such as dysarthria or cognitive disturbances. Additionally, lesions generally yield effects on only one side of the body (the contra-lateral side), and bilateral lesions are significantly more likely to produce side effects. Other surgical procedures, such as fetal tissue transplants, are costly and unproven.

High frequency chronic electrical stimulation (i.e., frequencies above about 50-100 Hz) of certain areas of the brain has been demonstrated to be as efficacious as producing a lesion in any one of those areas. In contrast to ablation surgery, chronic electrical stimulation is reversible. Additionally, stimulation parameters may be adjusted to minimize side effects while maintaining efficacy; such "fine tuning" is unavailable when producing a lesion. An implantable chronic stimulation device for deep brain stimulation (DBS) is available and similar systems are under development.

Vagus nerve stimulation (VNS) has been applied with partial success to patients with refractory epilepsy. In this procedure, an implantable pulse generator in implanted in the patient's thorax, and an electrode lead is routed from the IPG to the left vagus nerve in the neck. Helix-shaped stimulation and indifferent electrodes are attached to the vagus nerve via an invasive surgical process that requires the carotid sheath to be fully exposed. Based on a number of studies, approximately 5% of patients undergoing VNS are seizure-free, and an additional 30-40% of patients have a greater than 50% reduction in seizure frequency. However, VNS may lead to significant side effects. The vagus nerve provides parasympathetic innervation to the cardiac tissue, and thus VNS may lead to bradycardia, arrhythmia, or even graver cardiac side effects. In fact, VNS systems are only used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

The exact mechanism of action of VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker et al. applied muscimol, an agonist of the inhibitory neurotransmitter GABA, to the NTS in a murine model of epilepsy ["Regulation of limbic motor seizures by GABA and glutamate transmission in nucleus tractus solitarius," Epilepsia, 1999 August]. Muscimol applied to the NTS attenuated seizures in all seizure models tested, whereas muscimol applied to adjacent regions of NTS had no effect. Additionally, bicuculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. concludes that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nucleus) receives somatic sensory input from all cranial nerves, with much of its input coming from the vagus nerve.

In 2001, Handforth et al. studied whether VNS could suppress tremor in the harmaline tremor model in the rat [Handforth et al. "Suppression of harmaline-induced tremor in rats by vagus nerve stimulation." Movement Disorders, 2001 January; 16(1):84-8]. Animals were chronically implanted with helical leads around the left vagus nerve and a disk-shaped electrode positioned subcutaneously in the dorsal neck. Harmaline-induced tremor was recorded on a physiograph while each animal received a sequence of five 20-minute trials. Each trial consisted of five minutes of pre-stimulation baseline, five minutes of VNS, and ten minutes of post-stimulation. VNS significantly suppressed harmaline-induced tremor. The suppressive effect was present within the first minute of stimulation and was reproducible across the five trials of the study. The results of this study suggest that the central generator or expression of tremor in the harmaline animal model can be suppressed by VNS. This further suggests that VNS may be an effective therapy for ET and/or other movement disorders.

Additional and improved treatment options are needed for patients suffering from movement disorders.

BRIEF SUMMARY OF THE INVENTION

The invention disclosed and claimed herein provides systems and methods for introducing one or more stimulating drugs to the vagus nerve and/or its branches for treating or preventing movement disorders, as well as the symptoms and pathological consequences thereof. According to some embodiments of the invention, the stimulation increases excitement of the vagus nerve and/or its branches, thereby treating or preventing movement disorders. In some embodiments, electrical stimulation is applied together with the drug(s).

The treatment provided by the invention may be carried out by one or more system control units (SCUs). In some forms of an SCU, one or more infusion outlets and/or catheters are surgically implanted to infuse drug(s) from an implantable pump. As an optional addition, one or more electrodes are surgically implanted to provide electrical stimulation from an implantable signal/pulse generator (IPG). When necessary and/or desired, an SCU may provide both electrical stimulation and one or more stimulating drugs. In other forms of an SCU, a miniature implantable neurostimulator (a.k.a., a microstimulator), such as a Bionic Neuron (also referred to as a BION® microstimulator) or the like, is implanted. For instance, a BION SCU(s) may be implanted substantially or entirely within the carotid sheath. The systems of the invention may also include one or more sensors for sensing symptoms or other conditions that may indicate a needed treatment.

In some configurations, the SCU is implanted in a surgically-created opening in the thorax, abdomen, or above the buttocks. In some such configurations, one or more catheters and optional electrode leads attached to the SCU run subcutaneously to the vagus nerve and/or one or more branches of the vagus nerve. Any electrodes used for electrical stimulation may be arranged as an array on a thin implantable lead. The SCUs programmed to produce electrical stimulation may provide either monopolar electrical stimulation, e.g., using the SCU case as an indifferent electrode, or to produce bipolar electrical stimulation, e.g., using one of the electrodes of an electrode array as an indifferent electrode.

The SCU used with the present invention possesses one or more of the following properties, among other properties:

a pump and at least one outlet for delivering a drug or drugs to surrounding tissue;

optionally, at least one electrode for applying stimulating current to surrounding tissue;

electronic and/or mechanical components encapsulated in a hermetic package made from biocompatible material(s);

an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;

means for receiving and/or transmitting signals via telemetry; and means for receiving and/or storing electrical power within the SCU.

An SCU may operate independently, or in a coordinated manner with other implanted SCUs, other implanted devices, and/or with devices external to a patient's body. For instance, an SCU may incorporate means for sensing a patient's condition. Sensed information may be used to control the drug and/or optional electrical stimulation parameters of the SCU in a closed loop manner. The sensing and stimulating means may be incorporated into a single SCU, or a sensing means may communicate sensed information to at least one SCU with stimulating means.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
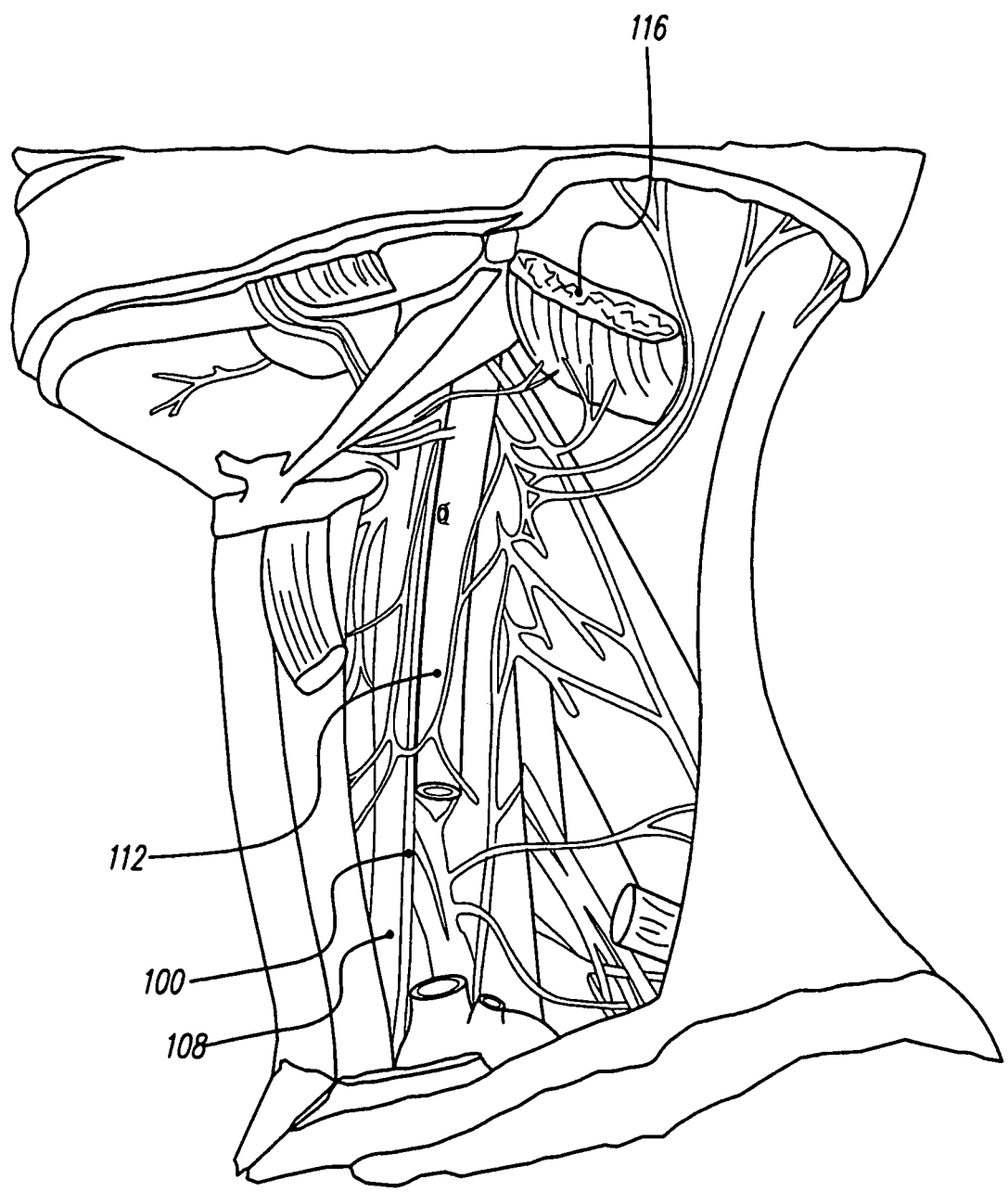
FIG. 1A depicts various nerves, muscles, arteries, and veins in the neck.
Figure 1B:
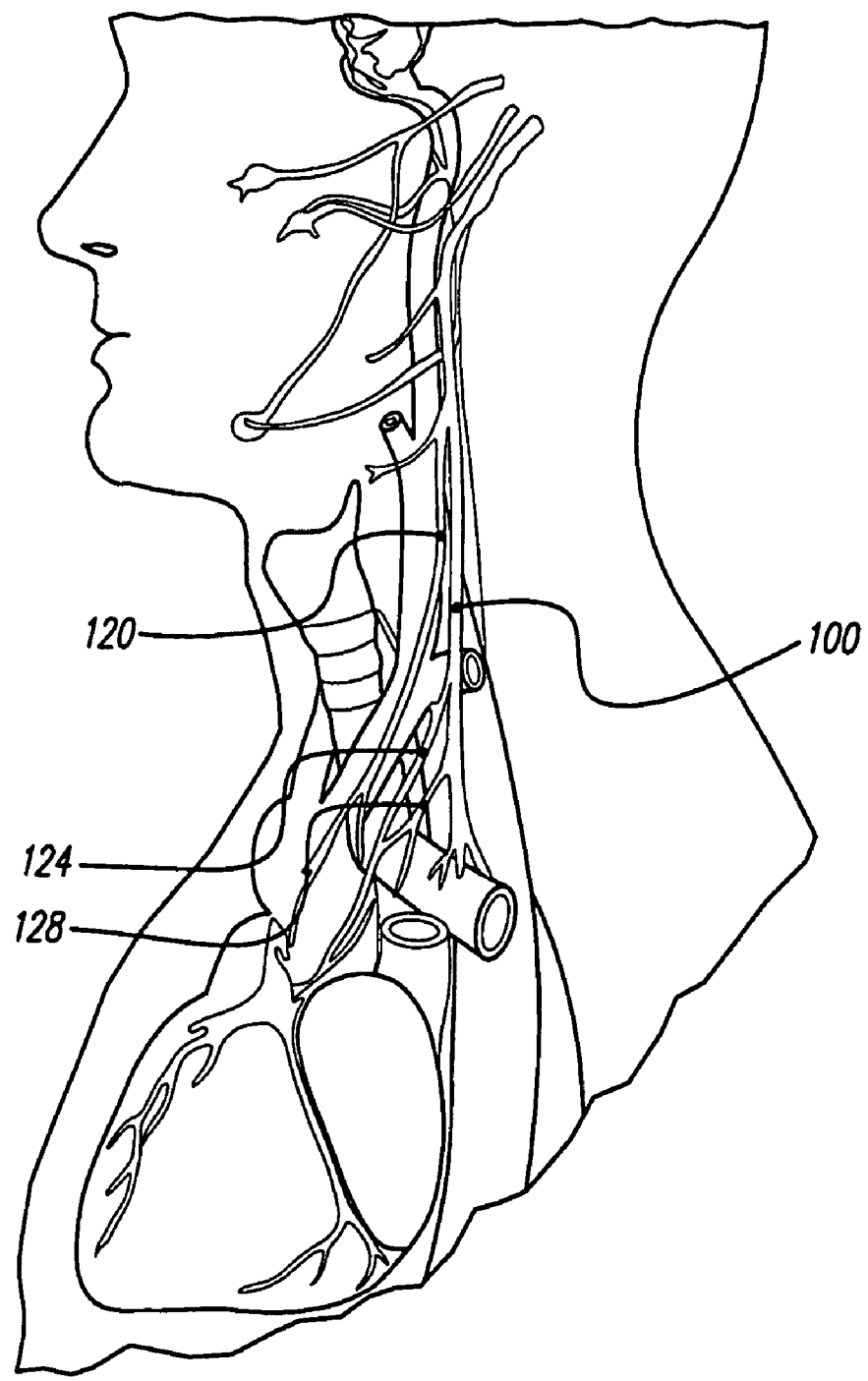
FIG. 1B illustrates various autonomic nerves in the head, neck, and thorax.

FIG. 1A depicts nerves, muscles, arteries, and veins in the neck, while FIG. 1B illustrates various nerves in the head, neck, and thorax. As can be seen, the vagus nerve 100 is relatively easily accessible in the neck. The vagus nerve lies within the carotid sheath 104, along with the common carotid artery 108 and the internal jugular vein 112. The carotid sheath 104 lies beneath the sternocleidomastoid muscle 116, which, in FIG. 1A, is cut and turned up.

Figure 2:
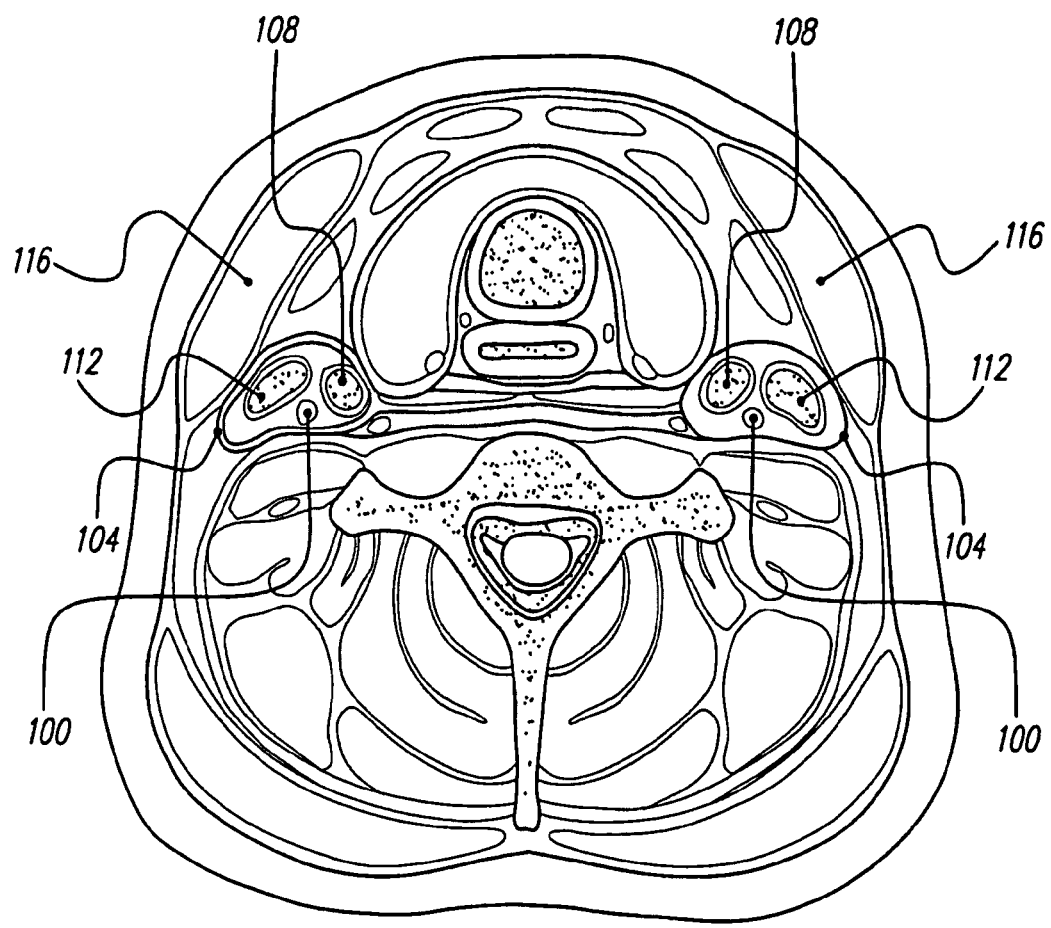
FIG. 2 is a cross-section through the neck, at the level of cervical vertebra C7.

FIG. 2 is a cross-section through the neck, at the level of cervical vertebra C7. The vagus nerve 100 has a number of nerve branches. Three of these branches are named the superior cervical cardiac branch 120, the inferior cervical cardiac branch 124, and the thoracic cardiac branch 128. Advantageously, these and other branches are sufficiently separate from vagus nerve 100 to allow independent and selective stimulation of vagus nerve 100 and/or its various branches via appropriate placement of infusion outlet(s) and optional electrode(s) of an SCU. Reference is made herein to "at least one vagus nerve" when indicating either of the left and/or right vagus nerve 100 and/or branches of the left and/or right vagus nerve.

Thus, as described in more detail herein, the present invention provides stimulating drugs, with the optional addition of electrical stimulation, to stimulation site(s) on the left vagus nerve, the right vagus nerve, and/or branches thereof. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

Herein, stimulating drugs comprise medications and other pharmaceutical compounds, anesthetic agents, synthetic or natural hormones, neurotransmitters, interleukins, cytokines, lymphokines, chemokines, growth factors, neural depolarizing agents, and other intracellular and intercellular chemical signals and messengers, and the like. Certain hormones, neurotransmitters, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

Figure 3:
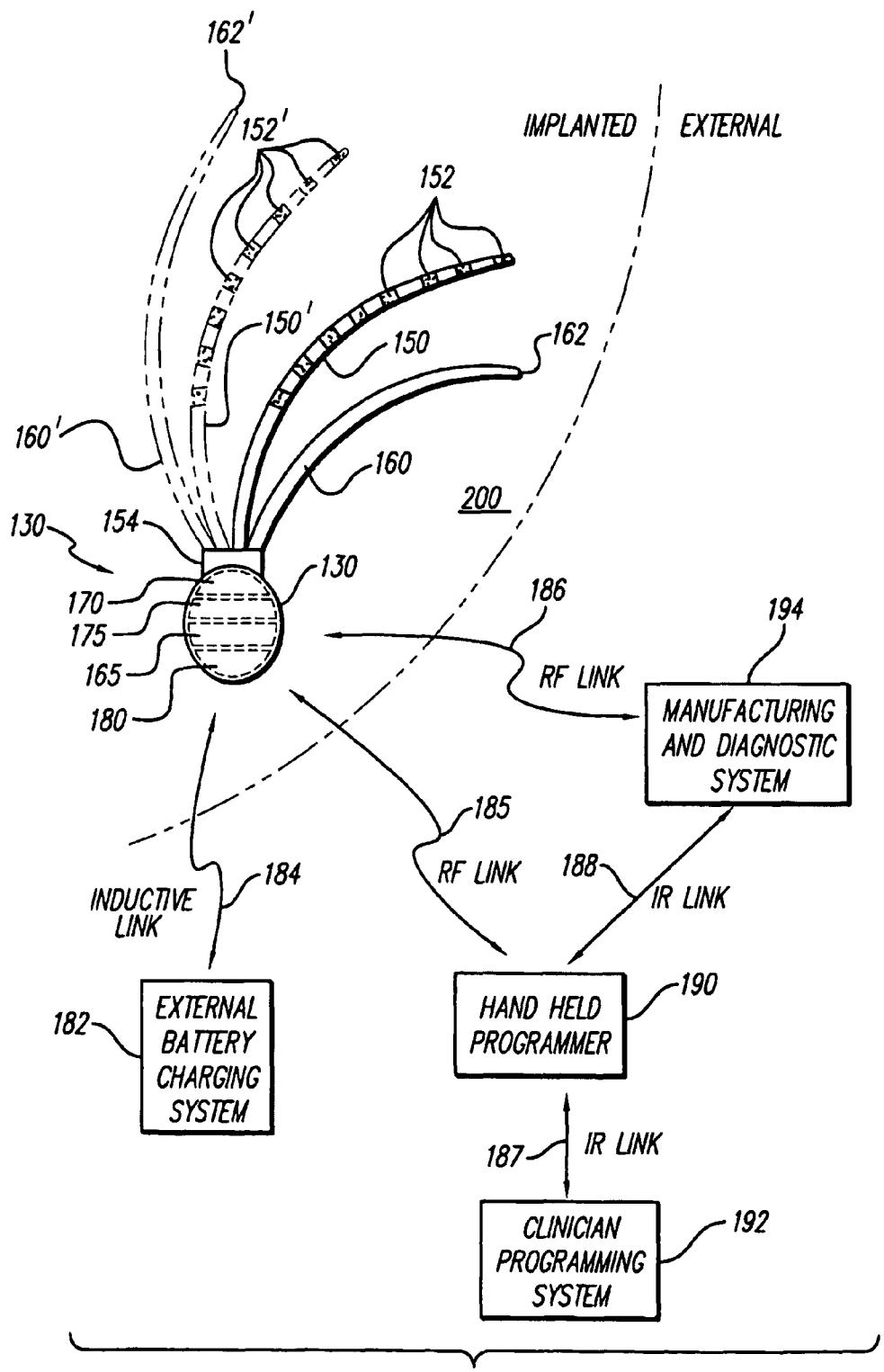
FIG. 3 illustrates internal and external components of certain embodiments of the invention.

The treatment is carried out by a system control unit (SCU) comprising an implantable pump that is coupled to a catheter having a discharge portion for infusing therapeutic dosages of the one or more drugs to a treatment site (see FIG. 3). Additionally or alternatively, a small implantable device with infusion outlets may be implanted at or near the treatment site (see FIGS. 4A-4C). Such a device is taught in U.S. patent application Ser. No. 10/057,144, filed Jan. 24, 2002, which application is incorporated herein by reference.

In some alternatives, optional additional electrical stimulation is provided by an SCU that is or includes an implantable signal generator connected to an electrode(s) for electrically stimulating a treatment site. The signal generator may be coupled to a lead with electrode(s) positioned at the treatment site, such as shown in FIG. 3, or may be a small implantable device, such as a BION® microstimulator or the like, implanted at or near the treatment site. The following documents describe various details associated with the manufacture, operation and use of BION implantable microstimulators, and are all incorporated herein by reference:

| Patent/<br>Publication No. | Filing/Publication<br>Date | Title |
| --- | --- | --- |
| U.S. Pat. No. 5,193,539 | Issued: Mar. 16, 1993 | Implantable Microstimulator |
| U.S. Pat. No. 5,193,540 | Issued: Mar. 16, 1993 | Structure and Method of Manufacture of an Implantable Microstimulator |
| U.S. Pat. No. 5,312,439 | Issued: May 17, 1994 | Implantable Device Having an Electrolytic Storage Electrode |
| WO 98/37926 | Published: Sep. 03, 1998 | Battery-Powered Patient Implantable Device |
| WO 98/43700 | Published: Oct. 08, 1998 | System of Implantable Devices For Monitoring and/or Affecting Body Parameters |
| WO 98/43701 | Published: Oct. 08, 1998 | System of Implantable Devices For Monitoring and/or Affecting Body Parameters |
| U.S. Pat. No. 6,051,017 | Issued: Apr. 18, 2000 | Improved Implantable Microstimulator and Systems Employing Same |
|  | Published: September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781-790. |

Thus, therapy is provided in accordance with the teachings of the present invention by infusion of one or more stimulating drugs, with the optional addition of electrical stimulation, by one or more system control units (SCUs). In the case of drug infusion only, an SCU comprises an implantable pump or the like. For the optional electrical stimulation, SCUs include a microstimulator and/or an implantable pulse/signal generator (IPG), or the like. In cases requiring electrical stimulation in addition to drug infusion, more than one SCU is used. Alternatively, when needed and/or desired, an SCU provides one or more stimulating drugs and electrical stimulation.

As seen in the embodiments depicted in FIG. 3, SCU 130 may be surgically implanted, for instance, in the thorax, abdomen, or above the buttocks, while one or more catheters 160 attached to SCU 130 run subcutaneously in a surgically-created tunnel to the target site. Optionally, one or more electrode leads 150 may also be attached to SCU 130, with the electrodes tunneled to the target site. SCU 130, in the configuration of FIG. 3, may conform to the profile of surrounding tissue(s) and/or bone(s), and is small and compact. This may minimize pressure applied to the skin or other tissue, which pressure may result in skin erosion or infection. In various embodiments, SCU 130 has a diameter of about 75 mm, or only about 65 mm, or even less than about 55 mm. In such configurations, SCU thickness may be about 10-12 mm, or even less than about 10 mm. Small size and recessed placement of the SCU and catheter(s) and/or lead(s) decreases the likelihood of erosion of the overlying skin, and minimizes any cosmetic impact.

Figure 4A:
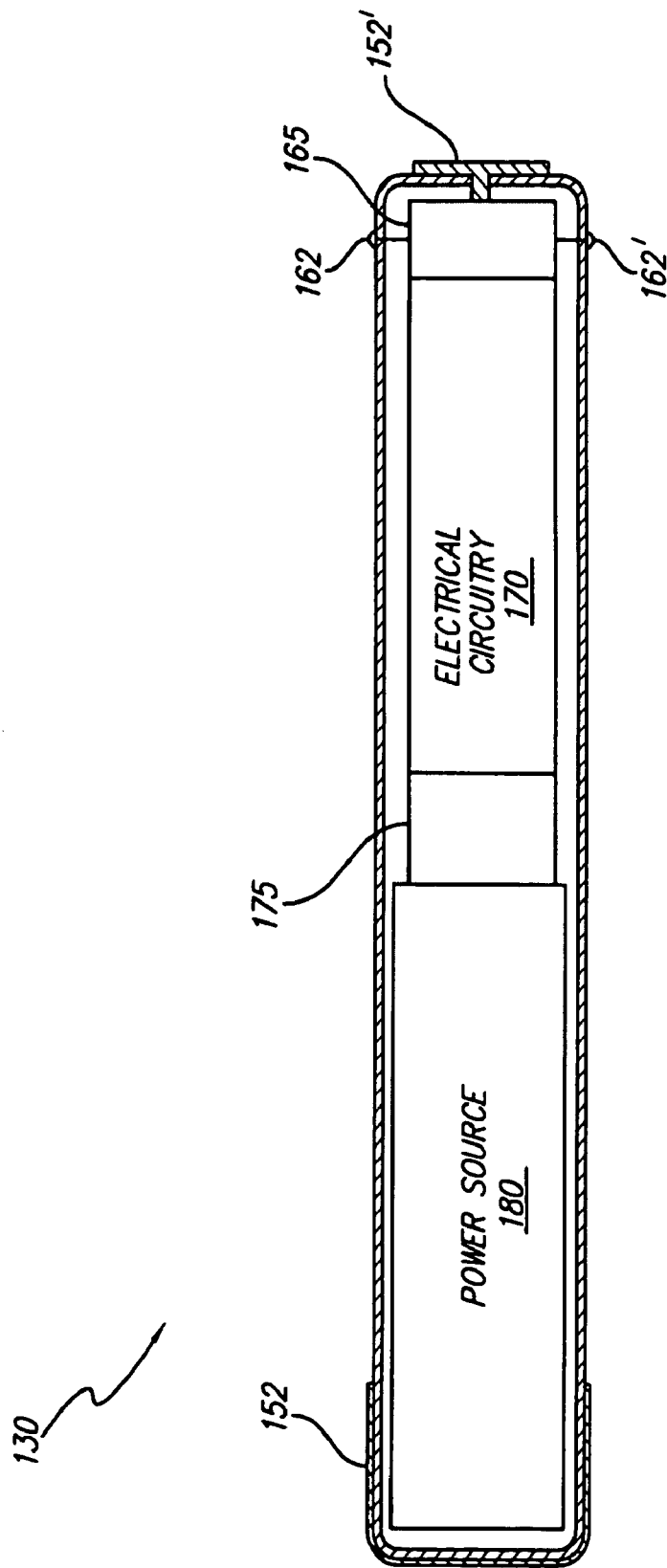
FIGS. 4A, 4B, and 4C show possible configurations of an implantable microstimulator of the present invention.
Figure 4B:
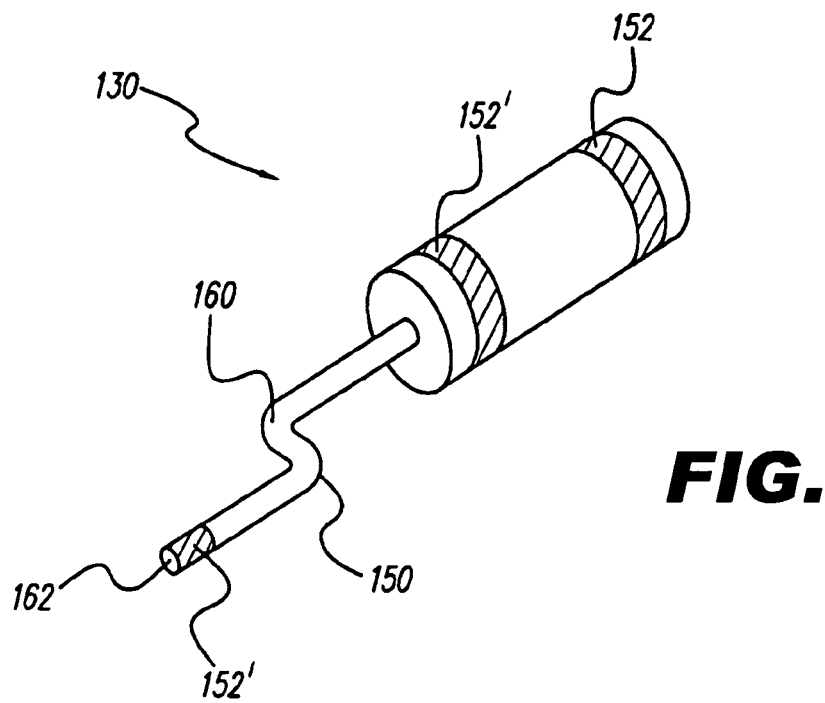
Figure 4C:
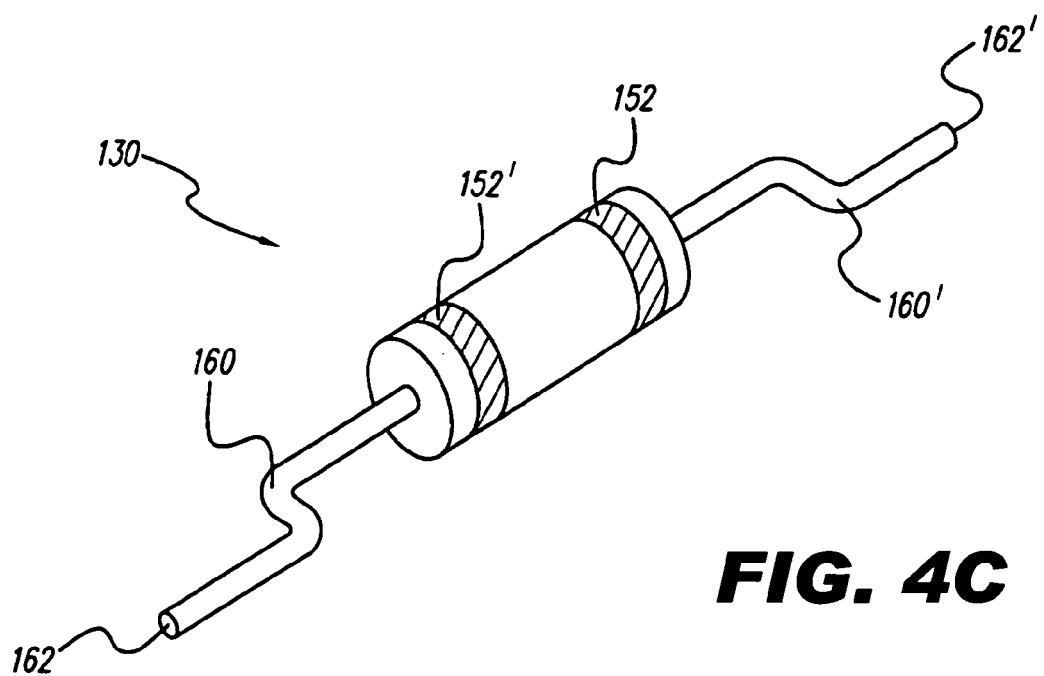

Certain configurations of SCU 130 are sufficiently small to permit placement in, adjacent, or near the structure(s) to be stimulated. As shown in FIGS. 4A, 4B, and 4C, SCU 130 may be a microstimulator in the form of a narrow, elongated capsule. For instance, the microstimulator capsule may have a diameter of about 4-5 mm, or only about 3 mm, or even less than about 3 mm. Capsule length may be about 25-35 mm, or only about 20-25 mm, or even less than about 20 mm. The shape of the microstimulator may be determined by the structure of the desired target, the surrounding area, and the method of implantation. A thin, elongated cylinder, as shown in FIGS. 4A, 4B, and 4C, is one possible configuration, but other shapes, such as cylinders, disks, spheres, and helical structures, are possible, as are additional catheters, infusion outlets, leads, and/or electrodes.

Microstimulator SCU 130 may be implanted with a surgical tool such as a tool specially designed for the purpose, or with a hypodermic needle, or the like. Alternatively, microstimulator SCU 130 may be implanted via conventional surgical methods (e.g., via a small incision), or may be placed using endoscopic or laparoscopic techniques. A more complicated surgical procedure may be required, e.g., for fixing the microstimulator in place.

In certain embodiments of the instant invention, SCU 130 includes infusion outlets 162/162' built into the SCU case, as shown in FIG. 4A. Optional electrodes 152/152' may be leadless electrodes built into or attached to the SCU case, as shown in FIGS. 4A-4C. As detailed in the referenced patent publications, optional electrodes 152 and 152' generally comprise a stimulating electrode (to be placed close to the target tissue) and an indifferent electrode (for completing the circuit).

As seen in FIGS. 4B and 4C, microstimulator SCU 130 may additionally or alternatively include infusion outlet(s) 162/162' located at the ends of short, flexible catheter(s) 160/160' and/or leads 150/150' which may optionally include electrode(s) 152/152' as described in U.S. patent application Ser. No. 09/624,130, filed Jul. 24, 2000, which application is incorporated herein by reference in its entirety. The use of such catheters or leads permits, among other things, infused drugs and optional electrical stimulation to be directed more locally to targeted tissue(s) a short distance from the surgical fixation of the bulk of microstimulator SCU 130, while allowing most elements of the microstimulator to be located in a more surgically convenient site. This minimizes the distance traversed and the surgical planes crossed by the device and any catheter(s)/lead(s). In most uses of this invention, the catheters and leads are no longer than about 150 mm.

SCU 130 (which herein refers to implantable pumps, pump/IPG combinations, microstimulators for drug and/or electrical stimulation, and/or other alternative devices described herein) contains at least one pump 165 for storing and dispensing one or more drugs through outlet(s) 162/162' and/or catheter(s) 160/160'. When a catheter is used, it includes at least one infusion outlet 162, usually positioned at least at a distal end, while a proximal end of the catheter is connected to SCU 130.

In the case of treatment additionally constituting electrical stimulation, in some embodiments such as depicted in FIG. 3, electrode(s) 152 are carried on lead 150 having a proximal end coupled to SCU 130, via connector 154 if necessary. As known in the art, the lead contains insulated wires electrically connecting electrodes 152 to SCU 130. SCU 130 contains electrical components 170 that produce electrical stimulation pulses that travel through the wires of lead 150 and are delivered to electrodes 152, and thus to the tissue surrounding electrodes 152.

To protect the electrical components inside SCU 130, some or all of the case of the SCU may be hermetically sealed. Glass, ceramic, or other material that provides a hermetic package that excludes water vapor but permits passage of electromagnetic fields used to transmit data and/or power may be used. For additional protection against, e.g., impact, the case may be made of metal (e.g. titanium) or ceramic, which materials are also, advantageously, biocompatible. In addition, SCU 130 may be configured to be Magnetic Resonance Imaging (MRI) compatible. Electrodes 152/152', when used, may be made of a noble or refractory metal or compound, such as platinum, iridium, tantalum, titanium, titanium nitride, niobium or alloys of any of these, in order to avoid corrosion or electrolysis which could damage the surrounding tissues and the device.

According to some embodiments of the invention, such as depicted in FIG. 3, at least one catheter 160 is attached to SCU 130, via a suitable connector 154, if necessary. One or more optional leads include at least one electrode 152, and may include as many as sixteen or more electrodes 152. Additional catheter(s) 160' and/or leads 150' may be attached to SCU 130. Hence, FIG. 3 shows (in phantom lines) a second catheter 160', and a second lead 150', having electrodes 152' thereon, also attached to SCU 130. Similarly, the SCU 130 of FIGS. 4A, 4B, and 4C have outlets 162, 162' for infusing a stimulating drug(s) and optional electrodes 152, 152' for applying electrical stimulation.

Substantially cylindrical catheter(s) 160 and lead(s) 150 of certain embodiments of the present invention may be less than 5 mm in diameter, or even less than about 1.5 mm in diameter. In embodiments using one or more paddle-shaped leads, lead(s) 150 may be less than 15 mm in width, and less than 1.5 mm in thickness. Electrodes 152, 152' on leads 150, 150' may be arranged as an array, for instance, as two or more collinear electrodes, or even as four or more collinear electrodes, or they may not be collinear. A tip electrode may also be supplied at the distal end of one or more leads.

In some embodiments using optional electrical stimulation, SCU 130 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 130 have at least four channels and drive up to sixteen electrodes or more.

SCU 130 contains, when necessary and/or desired, electronic circuitry 170 for receiving data and/or power from outside the body by inductive, radio frequency (RF), or other electromagnetic coupling. In some embodiments, electronic circuitry 170 includes an inductive coil for receiving and transmitting RF data and/or power, an integrated circuit (IC) chip for decoding and storing stimulation parameters and generating drug or electrical stimulation pulses (either intermittent or continuous), and additional discrete electronic components required to complete the electronic circuit functions, e.g. capacitor(s), resistor(s), coil(s), and the like.

SCU 130 also includes, when necessary and/or desired, a programmable memory 175 for storing a set(s) of data, stimulation, and control parameters. Among other things, memory 175 may allow electrical and/or drug stimulation to be adjusted to settings that are safe and efficacious with minimal discomfort for each individual. Specific parameters may provide therapeutic advantages for various types and severities of movement disorders. For instance, some patients may respond favorably to intermittent stimulation, while others may require continuous treatment for relief. In some embodiments, drug stimulation and electrical stimulation parameters are controlled independently, e.g., continuous drug stimulation and no electrical stimulation. However, in some instances, they may advantageously be coupled, e.g., electrical stimulation may be programmed to occur only during drug infusion.

In addition, different stimulation parameters may have different effects on neural tissue. Therefore, parameters may be chosen to target specific neural populations and/or to exclude others, or to increase neural activity in specific neural populations and/or to decrease neural activity in others. For example, excitatory neurotransmitters (e.g., acetylcholine, glutamate, glutamate receptor agonist(s), dopamine, norepinephrine, epinephrine, serotonin), agonists thereof (e.g., acetylcholine receptor agonist such as bethanechol), and agents that act to increase levels of an excitatory neurotransmitter(s) (e.g., edrophonium, Mestinon) generally have an excitatory effect on neural tissue, while inhibitory neurotransmitters (e.g., dopamine, glycine, and gamma-aminobutyric acid, a.k.a. GABA), agonists thereof (e.g., benzodiazepines, such as diazepam, or barbiturates), and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. prazosin, metoprolol) and agents that decrease levels of excitatory neurotransmitter(s) (e.g., acetylcholinesterase) may inhibit neural activity. In addition, relatively low frequency neurostimulation (i.e., less than about 50-100 Hz) typically has an excitatory effect on surrounding neural tissue, leading to increased neural activity, whereas relatively high frequency neurostimulation (i.e., greater than about 50-100 Hz) may have an inhibitory effect, leading to decreased neural activity.

Some embodiments of SCU 130 also include a power source and/or power storage device 180. Possible power options for a stimulation device of the present invention, described in more detail below, include but are not limited to an external power source coupled to the stimulation device, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as shown in FIG. 3, SCU 130 includes a rechargeable battery as a power source/storage device 180. The battery is recharged, as required, from an external battery charging system (EBCS) 182, typically through an inductive link 184. In these embodiments, SCU 130 includes a processor and other electronic circuitry 170 that allow it to generate stimulation pulses that are applied to the patient 200 through outlet(s) 162 and optional electrodes 152 in accordance with a program and stimulation parameters stored in programmable memory 175. As stated earlier, stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), and/or other device(s) external to the patient's body. For instance, an SCU may control or operate under the control of another implanted SCU(s), other implanted device(s), and/or other device(s) external to the patient's body. An SCU may communicate with other implanted SCUs, other implanted devices, and/or devices external to a patient's body via, e.g., an RF link, an ultrasonic link, a thermal link, and/or an optical link. Specifically, an SCU may communicate with an external remote control (e.g., patient and/or physician programmer) that is capable of sending commands and/or data to an SCU and that may also be capable of receiving commands and/or data from an SCU.

For example, as depicted in FIG. 3, some embodiments of SCU 130 of the present invention may be activated and deactivated, programmed and tested through a hand held programmer (HHP) 190 (which may also be referred to as a patient programmer and may be, but is not necessarily, hand held), a clinician programming system (CPS) 192 (which may also be hand held), and/or a manufacturing and diagnostic system (MDS) 194 (which may also be hand held). HHP 190 may be coupled to SCU 130 via an RF link 185. Similarly, MDS 194 may be coupled to SCU 130 via another RF link 186. In a like manner, CPS 192 may be coupled to HHP 190 via an infra-red link 187; and MDS 194 may be coupled to HHP 190 via another infra-red link 188. Other types of telecommunicative links, other than RF or infra-red may also be used for this purpose. Through these links, CPS 192, for example, may be coupled through HHP 190 to SCU 130 for programming or diagnostic purposes. MDS 194 may also be coupled to SCU 130, either directly through RF link 186, or indirectly through the IR link 188, HHP 190, and RF link 185.

In certain embodiments, using, for example, a microstimulator SCU 130 as described above and as illustrated in FIG. 5, the patient 200 switches SCU 130 on and off by use of controller 210, which may be handheld. SCU 130 is operated by controller 210 by any of various means, including sensing the proximity of a permanent magnet located in controller 210, sensing RF transmissions from controller 210, or the like.

Figure 5:
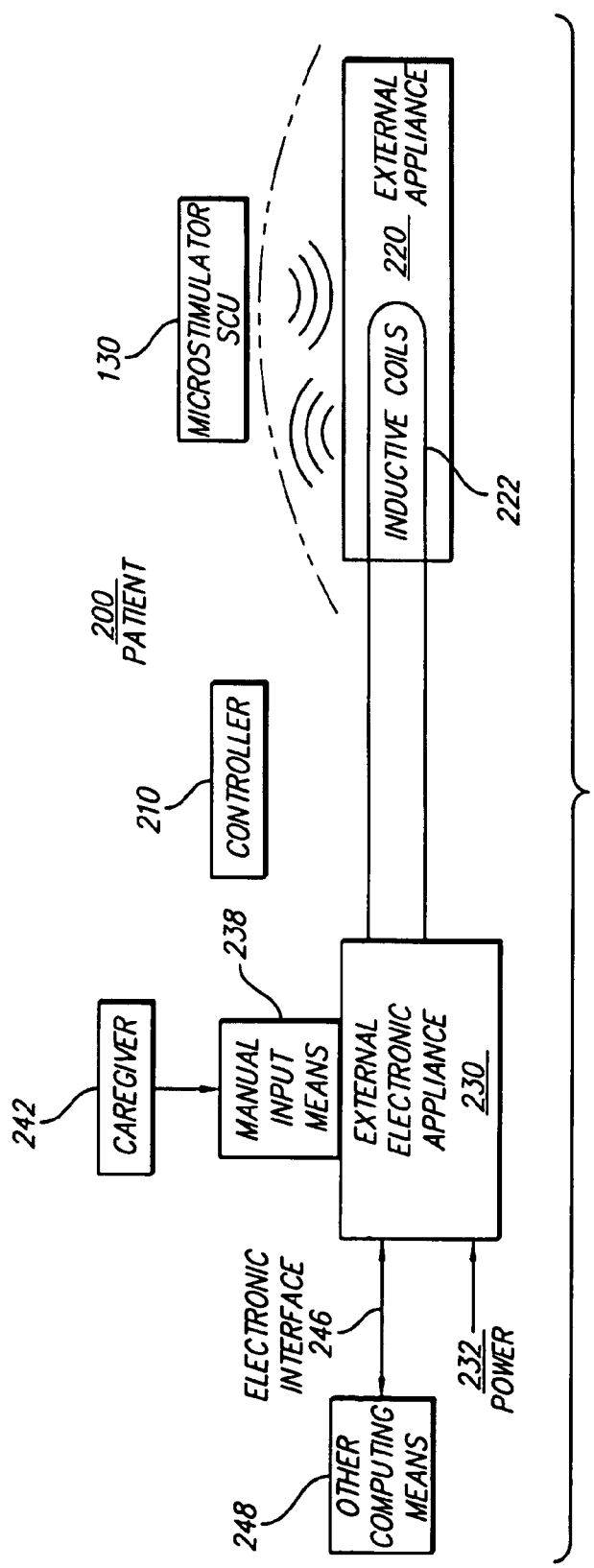
FIG. 5 illustrates external components of various embodiments of the invention.

External components for programming and/or providing power to various embodiments of SCU 130 are also illustrated in FIG. 5. When communication with such an SCU 130 is desired, patient 200 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 200 or a caregiver 242 may request changes in electrical and/or drug stimulation parameters produced during the normal operation of SCU 130. In these embodiments, manual input means 238 includes various electro-mechanical switches and/or visual display devices that provide the patient and/or caregiver with information about the status and prior programming of SCU 130.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

One or more of the external appliance(s) may be embedded in a cushion, pillow, garment, or the like. Other possibilities exist, including a strap, band, patch, or other structure(s) that may be affixed to the patient's body or clothing. External appliances may include a package that can be, e.g., worn on the belt, may include an extension to a transmission coil affixed, e.g., with a Velcro® band or an adhesive, or may be combinations of these or other structures able to perform the functions described herein.

In order to help determine the amount and/or type(s) of stimulating drug(s) and/or the strength and/or duration of optional electrical stimulation required to produce the desired effect, in some embodiments, a patient's response to and/or need for treatment is sensed. For example, when infusion outlet(s) and/or electrodes of SCU 130 are implanted on or near a vagus nerve in the neck, EMG signals recorded from muscles in the neck may be sensed by an electrode(s) built into SCU 130 and may be recorded by SCU 130. The EMG may show a rhythmic oscillation that may indicate tremor, e.g., tremor of the head. (As used herein, "near" and "adjacent" mean as close as reasonably possible to targeted tissue, including touching or even being positioned within or attached to the tissue, or fixed to nearby tissue, but in general, may be as far as about 150 mm from the target tissue.)

Alternatively, an "SCU" dedicated to sensory processes communicates with an SCU providing stimulation pulses. The implant circuitry 170 may, if necessary, amplify and transmit these sensed signals, which may be digital or analog. Besides measuring EMG, other methods of determining the required drug stimulation or optional electrical stimulation include measuring neurotransmitter levels and/or their associated breakdown product levels, hormone levels, or other substances, such as dopamine levels, interleukins, cytokines, lymphokines, chemokines, growth factors, enzymes, medication and/or other drug levels, and/or levels of any other bloodborne substance(s), and/or changes in one or more of these may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). The EMG signal of a limb(s) may be measured as an indicator of limb tremor, sensed via EMG electrodes implanted in or placed adjacent to a limb muscle. An accelerometer may be attached to or implanted in a limb or other part of the body to sense motion that may be indicative or tremor. Other methods are mentioned herein, and yet others will be evident to those of skill in the field upon review of the present disclosure. The sensing may occur during stimulation (e.g., infusion) or during a temporary suspension of stimulation. The sensed information may be used to control stimulation parameters in a closed-loop manner.

For instance, in several embodiments of the present invention, a first and second "SCU" are provided. The second "SCU" periodically (e.g. once per minute) records limb electromyograph (EMG) activity, which it transmits to the first SCU. The first SCU uses the sensed information to adjust drug and/or electrical stimulation parameters according to an algorithm programmed, e.g., by a physician. For example, electric stimulation of the vagus nerve may be initiated or increased in response to increased rhythmic EMG activity. In some alternatives, one SCU performs both the sensing and stimulating functions, as discussed in more detail presently.

While an SCU 130 may also incorporate means of sensing symptoms or other prognostic or diagnostic indicators of movement disorders, e.g., via EMG or acceleration, it may alternatively or additionally be desirable to use a separate or specialized implantable device to record and telemeter physiological conditions/responses in order to adjust drug infusion and/or electrical stimulation parameters. This information may be transmitted to an external device, such as external appliance 220, or may be transmitted directly to implanted SCU(s) 130. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 130, and may be used to accomplish, potentially among other things, one or more of the following functions:

Function 1: If necessary, transmit electrical power from the external electronic appliance 230 via appliance 220 to SCU 130 in order to power the device and/or recharge the power source/storage device 180. External electronic appliance 230 may include an automatic algorithm that adjusts drug and/or electrical stimulation parameters automatically whenever the SCU(s) 130 is/are recharged.

Function 2: Transmit data from the external appliance 230 via the external appliance 220 to SCU 130 in order to change the parameters of drug and/or electrical stimulation used by SCU 130.

Function 3: Transmit sensed data indicating a need for treatment or in response to stimulation from SCU 130 (e.g., EMG, acceleration, neurotransmitter level, or other activity) to external appliance 230 via external appliance 220.

Function 4: Transmit data indicating state of the SCU 130 (e.g., battery level, drug level, stimulation parameters, etc.) to external appliance 230 via external appliance 220.

In another example, a treatment for movement disorders, e.g., essential tremor, may be carried out according to the following sequence of procedures:

1. An SCU 130 is implanted so that its infusion outlet 162 and possibly also electrodes 152 are located adjacent to the vagus nerve (e.g., a microstimulator may be located adjacent to a vagus nerve in the carotid sheath).
2. Using Function 2 described above (i.e., transmitting data) of external electronic appliance 230 and external appliance 220, SCU 130 is commanded to periodically infuse a fixed bolus of an excitatory neurotransmitter, e.g., bethanechol, or a neural depolarizing agent, e.g., succinylcholine, possibly while producing a series of excitatory electrical stimulation pulses, possible with gradually increasing amplitude.

3. After each infusion pulse, series of pulses, or at some other predefined interval, any change in tremor, sensed via EMG, acceleration, etc. resulting from the drug and/or electrical stimulation is sensed, for instance, by a sensor of SCU 130, which may be one or more electrodes 152 of SCU 130 acting as sensors. These responses are converted to data and telemetered out to external electronic appliance 230 via Function 3.
4. From the response data received at external appliance 230 from SCU 130, or from some other assessment, the stimulus threshold for obtaining a response is determined and is used by a clinician 242 acting directly 238 or by other computing means 248 to transmit the desired drug and/or electrical stimulation parameters to SCU 130 in accordance with Function 2.
5. When patient 200 desires to invoke drug infusion and/or electrical stimulation, patient 200 employs controller 210 to set SCU 130 in a state where it delivers a prescribed stimulation pattern from a predetermined range of allowable stimulation patterns.
6. To cease drug and/or electrical stimulation, patient 200 employs controller 210 to turn off SCU 130.
7. Periodically, the patient or caregiver recharges the power source/storage device 180 of SCU 130, if necessary, in accordance with Function 1 described above (i.e., transmit electrical power).

For the treatment of any of the various types and severities of movement disorders, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 130, each of which could be separately controlled by means of a digital address. Multiple channels and/or multiple patterns of drug and/or electrical stimulation might thereby be programmed by the clinician and controlled by the patient in order to, for instance, deal with complex or multiple symptoms or conditions, such as Parkinson's disease coupled with side effects from medication, e.g., dyskinesia.

In some embodiments discussed earlier, SCU 130, or a group of two or more SCUs, is controlled via closed-loop operation. A need for and/or response to stimulation is sensed via SCU 130, or by an additional SCU (which may or may not be dedicated to the sensing function), or by another implanted or external device. If necessary, the sensed information is transmitted to SCU 130. In some cases, the sensing and stimulating are performed by one SCU. In some embodiments, the parameters used by SCU 130 are automatically adjusted based on the sensed information. Thus, the electrical and/or drug stimulation parameters are adjusted in a closed-loop manner to provide stimulation tailored to the need for and/or response to the electrical and/or drug stimulation.

Figure 6:
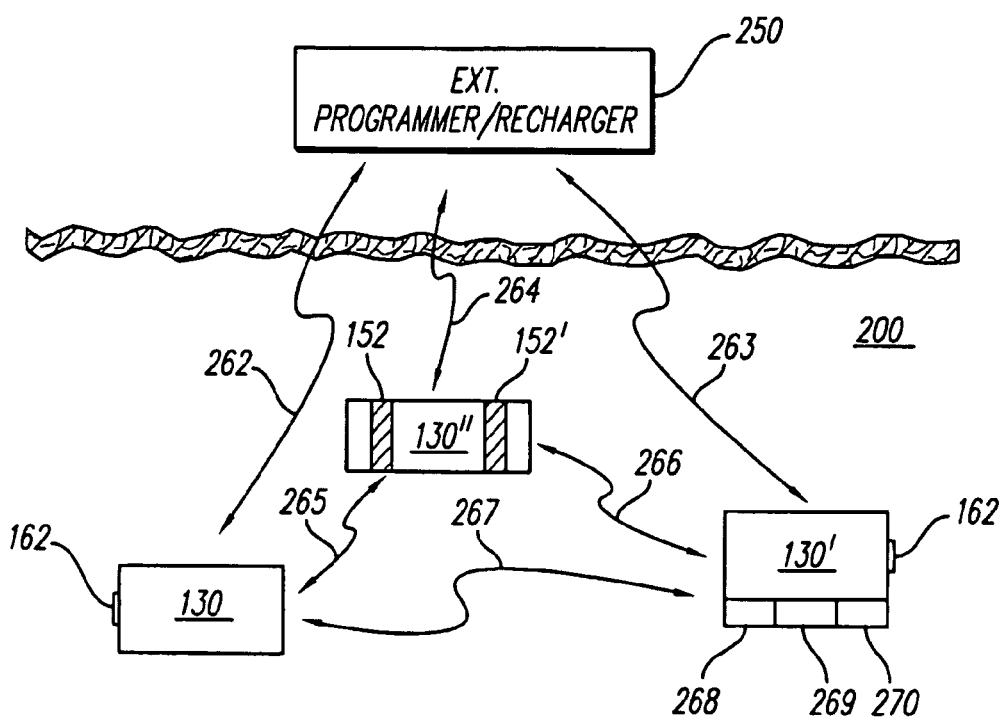
FIG. 6 depicts a system of implantable devices that communicate with each other and/or with external control/programming devices.

For instance, as shown in the examples of FIG. 6, a first SCU 130, implanted beneath the skin of the patient 200, provides a first medication or substance; a second SCU 130' provides a second medication or substance; and a third SCU 130" provides electrical stimulation via electrodes 152 and 152'. As mentioned earlier, the implanted devices may operate independently or may operate in a coordinated manner with other similar implanted devices, other implanted devices, or other devices external to the patient's body, as shown by the control lines 262, 263 and 264 in FIG. 6. That is, in accordance with certain embodiments of the invention, the external controller 250 controls the operation of each of the implanted devices 130, 130' and 130". According to various embodiments of the invention, an implanted device, e.g. SCU 130, may control or operate under the control of another implanted device(s), e.g. SCU 130' and/or SCU 130". That is, a device made in accordance with the invention may communicate with other implanted stimulators, other implanted devices, and/or devices external to a patient's body, e.g., via an RF link, an ultrasonic link, a thermal link, an optical link, or the like. Specifically, as illustrated in FIG. 6, SCU 130, 130', and/or 130", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects, clinical variables, or other indicators of the state of the patient, such as acceleration, EMG, EEG, or the like. The stimulator additionally or alternatively incorporates second means 269 for sensing neurotransmitter levels and/or their associated breakdown product levels, medication levels and/or other drug levels, hormone, enzyme, interleukin, cytokine, lymphokine, chemokine, and/or growth factor levels and/or changes in these or other substances in the blood plasma, local interstitial fluid, and/or cerebrospinal fluid. The stimulator additionally or alternatively incorporates third means 270 for sensing electrical current levels and/or waveforms supplied by another source of electrical energy, if necessary. Sensed information may be used to control infusion and/or electrical parameters in a closed loop manner, as shown by control lines 266, 267, and 265. Thus, the sensing means may be incorporated into a device that also includes drug and/or electrical stimulation, or the sensing means (that may or may not have stimulating means), may communicate the sensed information to another device(s) with stimulating means.

According to some embodiments of the invention, drug stimulation increases activity of afferent fibers of the vagus nerve 100 and/or of one or more vagus nerve branches, thereby treating or preventing movement disorders, such as essential tremor, and/or the symptoms and/or pathological consequences thereof. For example, the left vagus nerve may be stimulated below the superior cervical cardiac branch 120. Infusion with a neural depolarizing agent (e.g., succinylcholine), an excitatory neurotransmitter (e.g., acetylcholine), an excitatory neurotransmitter agonist (e.g., acetylcholine receptor agonist), an agent that acts to increase levels of an excitatory neurotransmitter, an inhibitory neurotransmitter antagonist, and/or an agent that acts to decrease levels of an inhibitory neurotransmitter is likely to produce such increased activity. As indicated earlier, some embodiments combine electrical stimulation with drug stimulation. In such embodiments, excitatory stimulation to cause increased activity is likely to be produced by relatively low-frequency electrical stimulation (e.g., less than about 50-100 Hz). As described earlier, this drug stimulation and optional electrical stimulation may be applied to one or more of the vagus nerves, such as vagus nerve 100 and/or a vagus nerve branch(es), to treat movement disorder(s).

In various embodiments, sensing means described earlier may be used to orchestrate first the activation of SCU(s) infusing stimulating drug(s) to an area(s) of a vagus nerve, and then, when appropriate, SCU(s) targeting another area(s) and/or by different means, e.g., applying electrical stimulation in combination with the drug stimulation. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method of operating an implantable stimulator to control a movement disorder, the method comprising:
    implanting a stimulator having at least one infusion outlet into a patient; and
    delivering at least one stimulus to at least one vagus nerve of the patient in accordance with one or more stimulation parameters configured to treat a movement disorder, wherein the at least one stimulus comprises at least one drug delivered through the at least one infusion outlet of the stimulator;
    wherein the at least one drug increases activity of the at least one vagus nerve in order to, at least in part, alleviate the movement disorder.

2. The method of claim 1, wherein the stimulator further includes at least two electrodes, and wherein the stimulus further comprises electrical stimulation delivered to the at least one vagus nerve via the at least two electrodes.

3. The method of claim 2, wherein the electrical stimulation is delivered at a frequency less than about 100 Hz.

4. The method of claim 1, wherein the at least one drug comprises a neural depolarizing agent.

5. The method of claim 4, wherein the neural depolarizing agent is succinylcholine.

6. The method of claim 1, wherein the at least one drug comprises at least one of an excitatory neurotransmitter, an excitatory neurotransmitter agonist, an inhibitory neurotransmitter antagonist, an agent that increases the level of an excitatory neurotransmitter, and an agent that decreases the level of an inhibitory neurotransmitter.

7. The method of claim 1, wherein the drug is at least one of acetylcholine and bethanechol.

8. The method of claim 1, further comprising sensing at least one condition and using the at least one sensed condition to automatically adjust one or more of the stimulation parameters governing the delivery of the at least one drug.

9. The method of claim 8, wherein the at least one sensed condition is one or more of acceleration, electromyographic activity, electrical activity of a neural population, a neurotransmitter level, change in a neurotransmitter level, a neurotransmitter breakdown product level, change in a neurotransmitter breakdown product level, a medication level, change in a medication level, a drug level, change in a drug level, a hormone level, change in a hormone level, an enzyme level, change in an enzyme level, an interleukin level, change in an interleukin level, a cytokine level, change in a cytokine level, a lymphokine level, change in a lymphokine level, a chemokine level, change in a chemokine level, a growth factor level, change in a growth factor level, level of a bloodborne substance, change in level of a bloodborne substance, level of a substance in the interstitial fluid, change in level of a substance in the interstitial fluid, a substance in the cerebrospinal fluid, and change in the level of a substance in the cerebrospinal fluid.

10. The method of claim 1, wherein said stimulator comprises a catheter, said catheter being connected to and extending from said stimulator and comprising said infusion outlet.

11. The method of claim 10, further comprising
    implanting the stimulator at a location remote from the at least one vagus nerve; and
    tunneling the catheter subcutaneously from the stimulator to the at least one vagus nerve.

12. The method of claim 1, wherein said movement disorder comprises at least one of Parkinson's disease and essential tremor.

13. The method of claim 10, further comprising delivering the at least one drug to the at least one vagus nerve via the catheter.

14. A method of treating a patient with a movement disorder, comprising:
    providing a stimulator;
    configuring one or more stimulation parameters to treat a movement disorder;
    programming said stimulator with said one or more stimulation parameters; and
    applying said stimulus with said stimulator to at least one vagus nerve within said patient in accordance with said one or more stimulation parameters;
    wherein said stimulus comprises at least one drug that increases activity of the at least one vagus nerve in order to at least in part alleviate said movement disorder.

15. The method of claim 14, wherein said stimulus further comprises electrical stimulation applied to said at least one vagus nerve.

16. The method of claim 14, wherein said at least one drug comprises a neural depolarizing agent.

17. The method of claim 16, wherein the neural depolarizing agent comprises succinylcholine.

18. The method of claim 14, wherein the at least one drug comprises at least one of an excitatory neurotransmitter, an excitatory neurotransmitter agonist, an inhibitory neurotransmitter antagonist, an agent that increases the level of an excitatory neurotransmitter, and an agent that decreases the level of an inhibitory neurotransmitter.

19. The method of claim 14, wherein the drug comprises at least one of acetylcholine and bethanechol.

20. The method of claim 14, further comprising sensing at least one condition and using the at least one sensed condition to automatically adjust one or more of the stimulation parameters.

* * * * *